(12) United States Patent
Bach et al.

(10) Patent No.: US 9,724,482 B2
(45) Date of Patent: Aug. 8, 2017

(54) NEBULIZER

(75) Inventors: Alexander Bach, Essen (DE); Jens Besseler, Bingen am Rhein (DE); Holger Holakovsky, Witten (DE); Markus Kaemper, Breckerfeld (DE); Manuel Krakowka, Welver (DE); Gilbert Wuttke, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 572 days.

(21) Appl. No.: 12/952,493

(22) Filed: Nov. 23, 2010

(65) Prior Publication Data

US 2011/0290239 A1 Dec. 1, 2011

(30) Foreign Application Priority Data

Nov. 25, 2009 (EP) ..................... 09014680

(51) Int. Cl.
*A61M 11/00* (2006.01)
*A61M 15/00* (2006.01)
*B05B 11/00* (2006.01)

(52) U.S. Cl.
CPC ...... *A61M 15/0065* (2013.01); *A61M 15/007* (2014.02); *A61M 15/0036* (2014.02); *A61M 15/0073* (2014.02); *A61M 15/0081* (2014.02); *A61M 2205/276* (2013.01); *B05B 11/309* (2013.01)

(58) Field of Classification Search
CPC ........ A61M 15/009; A61M 2016/0021; A61M 15/00; A61M 15/0065; A61M 15/0003–15/001; A61M 15/0021; A61M 15/0028; A61M 15/0033; A61M 15/0035–15/0041; A61M 15/0043; A61M 15/0045; A61M 15/0051; A61M 15/0086–15/0088; A61M 15/06; A61M 15/08–15/085
USPC ............. 128/200.17, 200.19, 200.14; 368/10
See application file for complete search history.

(56) References Cited

U.S. PATENT DOCUMENTS

| | | | |
|---|---|---|---|
| 1,828,864 A | 10/1931 | Hopkins | |
| 2,015,970 A | 10/1935 | Schoene | |
| 2,127,401 A | 8/1938 | Gillican | |
| 2,161,071 A | 6/1939 | McGrath et al. | |
| 2,321,428 A | 6/1943 | Schloz | |

(Continued)

FOREIGN PATENT DOCUMENTS

| | | |
|---|---|---|
| AU | 2005201364 A1 | 7/2006 |
| CA | 1094549 A | 1/1981 |

(Continued)

OTHER PUBLICATIONS

International Search Report and Written Opinion for PCT/EP2010/067902 mailed May 2, 2011.

(Continued)

*Primary Examiner* — Peter S Vasat
*Assistant Examiner* — Ned T Heffner
(74) *Attorney, Agent, or Firm* — Paula K. Wittmayer; Philip I. Datlow

(57) ABSTRACT

A nebulizer includes an insertable container and a counter device for counting operations of the nebulizer. The nebulizer can be opened for replacing the container. The counter devices blocks opening of the nebulizer until a predetermined number for operations has been reached.

17 Claims, 14 Drawing Sheets

(56) References Cited

U.S. PATENT DOCUMENTS

Figure 1:
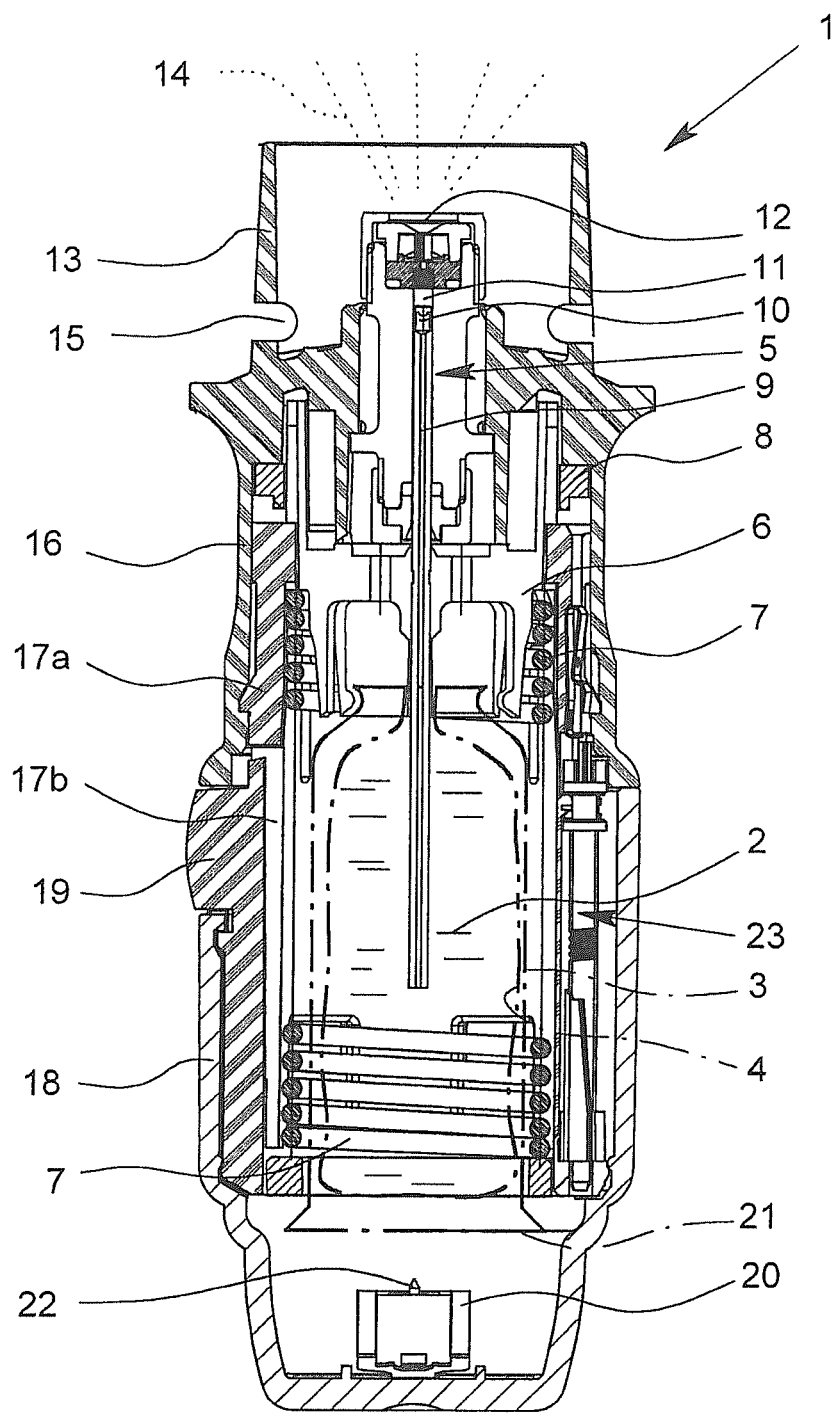

| | | |
|---|---|---|
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A * | 4/1997 | Jewett et al. ............ 128/200.23 |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |

(56) References Cited

U.S. PATENT DOCUMENTS

| | | |
|---|---|---|
| 5,950,016 A * | 9/1999 | Tanaka .............................. 396/6 |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Axford et al. |
| 6,548,647 B2 | 4/2003 | Dietz et al. |
| 6,550,477 B1 | 4/2003 | Lyon et al. |
| 6,565,743 B1 * | 5/2003 | Poirier et al. .................. 210/85 |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 * | 1/2004 | Rand et al. .............. 128/203.15 |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 * | 10/2001 | De La Huerga ............ 340/573.1 |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0007155 A1 | 1/2002 | Freund et al. |
| 2002/0046751 A1 | 4/2002 | MacRae et al. |
| 2002/0060255 A1 | 5/2002 | Benoist |

(56) References Cited

U.S. PATENT DOCUMENTS

| | | |
|---|---|---|
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1* | 11/2005 | Zierenberg et al. ..... 128/200.14 |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1* | 7/2006 | Lee et al. ................ 128/203.15 |
| 2006/0196500 A1 | 9/2006 | Hochrainer et al. |
| 2006/0225734 A1 | 10/2006 | Sagaser et al. |
| 2006/0239930 A1 | 10/2006 | Lamche et al. |
| 2006/0279588 A1* | 12/2006 | Yearworth et al. ................ 347/6 |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1* | 3/2007 | Geser et al. ............ 128/200.14 |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0272763 A1 | 11/2007 | Dunne et al. |
| 2007/0298116 A1 | 12/2007 | Bechtold-Peters et al. |
| 2008/0017192 A1* | 1/2008 | Southby et al. ........ 128/200.23 |
| 2008/0029085 A1 | 2/2008 | Lawrence et al. |
| 2008/0083408 A1* | 4/2008 | Hodson et al. .......... 128/200.23 |
| 2008/0092885 A1 | 4/2008 | von Schuckmann |
| 2008/0197045 A1 | 8/2008 | Metzger et al. |
| 2008/0249459 A1 | 10/2008 | Godfrey et al. |
| 2008/0265198 A1 | 10/2008 | Warby |
| 2008/0283553 A1 | 11/2008 | Cox et al. |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0221626 A1 | 9/2009 | Schmidt |
| 2009/0235924 A1* | 9/2009 | Holakovsky et al. ... 128/200.14 |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |

(56) References Cited

U.S. PATENT DOCUMENTS

| | | |
|---|---|---|
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0289336 A2 | 11/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2003511212 A | 3/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 8100674 A1 | 3/1981 |
| WO | 8200785 A1 | 3/1982 |
| WO | 8300288 A1 | 2/1983 |
| WO | 8303054 A1 | 9/1983 |
| WO | 8605419 A1 | 9/1986 |
| WO | 8706137 A1 | 10/1987 |
| WO | 8803419 A1 | 5/1988 |
| WO | 8900889 A1 | 2/1989 |
| WO | 8900947 A1 | 2/1989 |
| WO | 8902279 A1 | 3/1989 |
| WO | 8903672 A1 | 5/1989 |
| WO | 8903673 A1 | 5/1989 |
| WO | 8905139 A1 | 6/1989 |
| WO | 9009780 A1 | 9/1990 |
| WO | 9009781 A1 | 9/1990 |
| WO | 9114468 A1 | 10/1991 |
| WO | 9206704 A1 | 4/1992 |
| WO | 9217231 A1 | 10/1992 |
| WO | 9221332 A1 | 12/1992 |
| WO | 9222286 | 12/1992 |
| WO | 9313737 A1 | 7/1993 |
| WO | 9324164 A1 | 12/1993 |
| WO | 9325321 A1 | 12/1993 |
| WO | 9407607 A1 | 4/1994 |
| WO | 9417822 A1 | 8/1994 |
| WO | 9425371 A1 | 11/1994 |
| WO | 9427653 A2 | 12/1994 |
| WO | 9503034 A1 | 2/1995 |
| WO | 9532015 A1 | 11/1995 |
| WO | 9600050 A1 | 1/1996 |

(56) References Cited

FOREIGN PATENT DOCUMENTS

| | | |
|---|---|---|
| WO | 9606011 A2 | 2/1996 |
| WO | 9606581 A1 | 3/1996 |
| WO | 9623522 A1 | 8/1996 |
| WO | 9701329 A1 | 1/1997 |
| WO | 9706813 A1 | 2/1997 |
| WO | 9706842 A1 | 2/1997 |
| WO | 9712683 A1 | 4/1997 |
| WO | 9712687 A1 | 4/1997 |
| WO | 9720590 A1 | 6/1997 |
| WO | 9723208 A1 | 7/1997 |
| WO | 9727804 A1 | 8/1997 |
| WO | 9735562 A1 | 10/1997 |
| WO | 9741833 A1 | 11/1997 |
| WO | 9812511 A2 | 3/1998 |
| WO | 9827959 A2 | 7/1998 |
| WO | 9831346 A1 | 7/1998 |
| WO | 9839043 A1 | 9/1998 |
| WO | 9901227 A1 | 1/1999 |
| WO | 9907340 A1 | 2/1999 |
| WO | 9911563 A1 | 3/1999 |
| WO | 9916530 A1 | 4/1999 |
| WO | 9943571 A1 | 9/1999 |
| WO | 9962495 A2 | 12/1999 |
| WO | 9965464 | 12/1999 |
| WO | 99901520 A | 12/1999 |
| WO | 0001612 A2 | 1/2000 |
| WO | 0023037 A1 | 4/2000 |
| WO | 0023065 A2 | 4/2000 |
| WO | 0027543 A1 | 5/2000 |
| WO | 0033965 A1 | 6/2000 |
| WO | 0037336 A1 | 6/2000 |
| WO | 0049988 A2 | 8/2000 |
| WO | 0064779 A1 | 11/2000 |
| WO | 0113885 A1 | 3/2001 |
| WO | 0128489 A1 | 4/2001 |
| WO | 0164182 A2 | 9/2001 |
| WO | 0185097 A2 | 11/2001 |
| WO | 0187392 A2 | 11/2001 |
| WO | 0197888 A2 | 12/2001 |
| WO | 0198175 A1 | 12/2001 |
| WO | 0198176 A2 | 12/2001 |
| WO | 0204054 A1 | 1/2002 |
| WO | 0205879 A1 | 1/2002 |
| WO | 0217988 A2 | 3/2002 |
| WO | 0232899 A1 | 4/2002 |
| WO | 0234411 A1 | 5/2002 |
| WO | 02070141 A1 | 9/2002 |
| WO | 02089887 A1 | 11/2002 |
| WO | 03002045 A1 | 1/2003 |
| WO | 03014832 A1 | 2/2003 |
| WO | 03020253 A2 | 3/2003 |
| WO | 03022332 A2 | 3/2003 |
| WO | 03035030 A1 | 5/2003 |
| WO | 03037159 A2 | 5/2003 |
| WO | 03037259 A2 | 5/2003 |
| WO | 03049786 A2 | 6/2003 |
| WO | 03050031 A1 | 6/2003 |
| WO | 03053350 A2 | 7/2003 |
| WO | 03057593 A1 | 7/2003 |
| WO | 03059547 A1 | 7/2003 |
| WO | 03068299 A1 | 8/2003 |
| WO | 03087097 A1 | 10/2003 |
| WO | 03097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 2004033954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A1 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A1 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013110601 A1 | 8/2013 |
| WO | 2013152861 A1 | 10/2013 |
| WO | 2013152894 A1 | 10/2013 |
| WO | 2015018901 A1 | 2/2015 |
| WO | 2015018903 A1 | 2/2015 |

(56) References Cited

FOREIGN PATENT DOCUMENTS

| WO | 2015018904 A1 | 2/2015 |
|---|---|---|
| WO | 2015169431 A2 | 11/2015 |
| WO | 2015169732 A1 | 11/2015 |

OTHER PUBLICATIONS

"Activate". Collins English Dictionary, London: Collins, 2000, 2 pages. [Retrieved at http://search.credoreference.com/content/entry/hcengdict/activate/0 on Jun. 12, 2014].

"Lung Cancer". Merck Manual Home Edition, pp. 1-7. [Accessed at www.merck.com/mmhe/print/sec04/ch057/ch057a.html, on Jul. 28, 2010].

Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English for WO2009050978, 2009.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.
Bocci et al., "Pulmonary catabolism of interferons: alveolar absorption of 125l-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.
Gras et al., "Comparison of chemical cleaning methods of glass in preparation for silanization". Biosensors & Bioelectronics, vol. 14, 1999, pp. 683-688.

Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.

\* cited by examiner

NEBULIZER

The present invention relates to a nebulizer.

One starting point for the present invention is a nebulizer illustrated in WO 2006/125577 A2. The nebulizer comprises, as a reservoir for fluid which is to be atomized or nebulizer, an insertable rigid container having an inner bag containing the fluid and a pressure generator with a drive spring for delivering and atomizing the fluid. Preferably, the container is secured against removal. For the purpose, the nebulizer of its housing may be designed such that it can not be opened after the container has been inserted.

Preferably, the container is pre-installed in nebulizer in the delivery state. In particular, the pre-installed container is held by a transportation lock unmovable within the housing in the delivery state in order to avoid any undesired opening of the container.

Before being used for the first time the nebulizer is completely closed. Thus, the pre-installed container is opened by a delivery tube piercing a sealing and a septum to fluidically connect to the inner bag of the container. Further, the transportation lock is opened so that the container can move inside the nebulizer back and forth.

By rotating the lower housing part of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a locking element the drive spring is released and the fluid in the pressure chamber is put under pressure by the drive spring and is delivered or atomized through a nozzle into a mouthpiece as an aerosol, without the use of propellant gas.

WO 2007/022898 A2 discloses a similar nebulizer. A container can be inserted into a housing of the nebulizer. The housing is closed by a lower or bottom housing part. The container is moving axially forth and back during conveying of the fluid to be nebulized, during pressure generation and/or during nebulization. A counter device can be arranged in the housing part. The counter device locks the nebulizer against further use if a predetermined number of operations has been reached or exceeded. Then, the housing part may be replaced together with the counter device and the container. The container may be connected inseparably with the housing part. Further, the nebulizer comprises a monitoring device for permanently locking the nebulizer when a certain number of containers has been used or when a certain number of operations has been reached.

Object of the present invention is to provide a nebulizer which can be used only with a predefined number of replaceable containers wherein a simple construction is possible and/or a defined handling is achieved.

The above object is achieved by a nebulizer as described herein. Preferred embodiments are also described herein.

The present invention relates to a nebulizer which can be opened for inserting and replacing a container with the fluid to be nebulized. The nebulizer comprises a counter device for counting operations of the nebulizer. The counter device blocks opening of the nebulizer until a predetermined number of operations has been reached or exceeded. Thus, it can be prevented that the nebulizer is opened before the container has been (sufficiently) used or has been emptied. Thus, potential soiling of the nebulizer can be minimized and/or a defined handling can be secured.

The nebulizer or counter device is preferably constructed such that the empty or used container is blocked against reuse and/or reconnection with the nebulizer. Thus, reuse of an already used container can be avoided.

Preferably, the nebulizer comprises a lower housing part which can be removed for opening the nebulizer and replacing the container. In particular, the counter device is arranged in the lower housing part and the container cannot be separated from the lower housing part so that these components have to be replaced altogether when the container is replaced. Thus, it is easy to prevent the use of an already used container as it cannot be reused due to its associated counter device.

Figure 2:
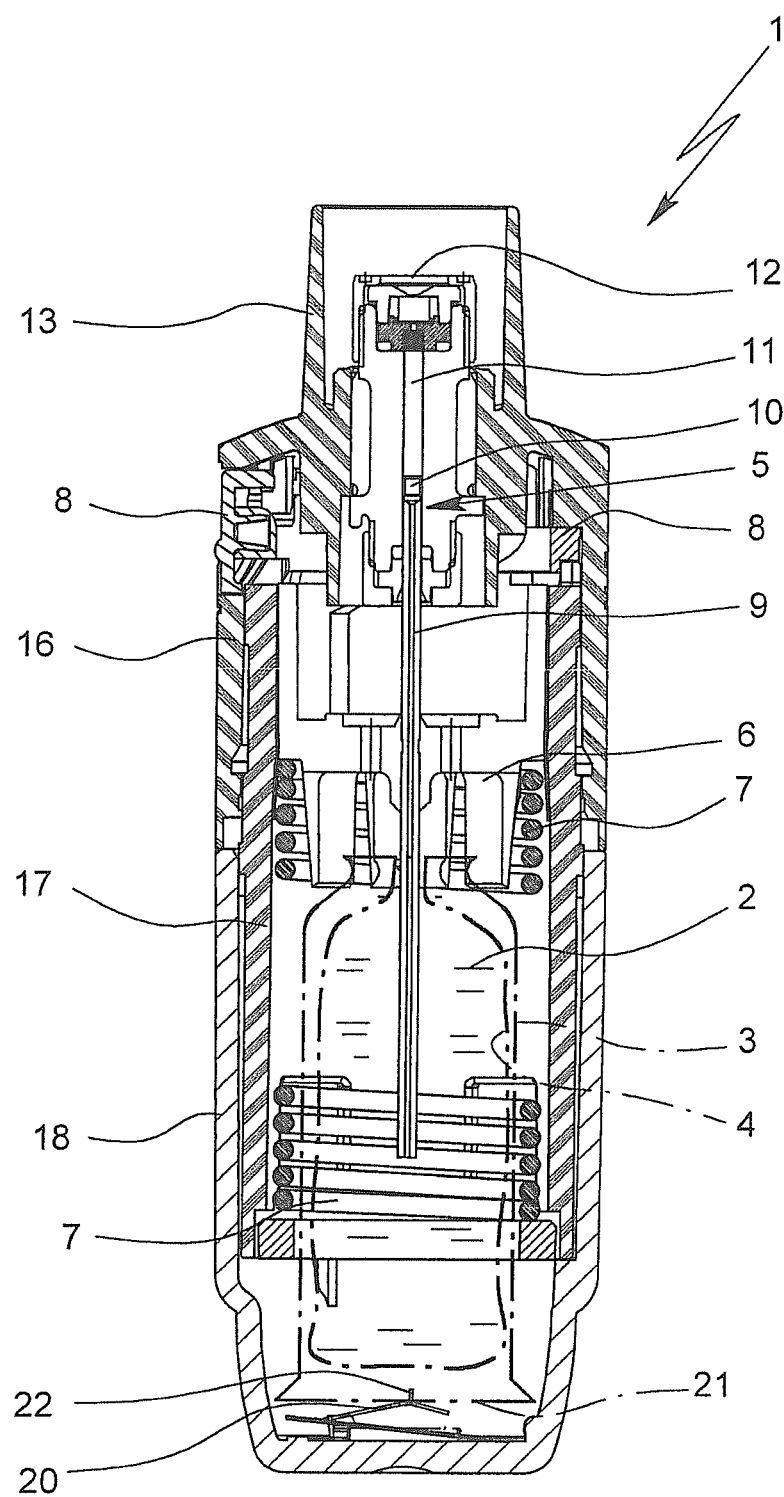
Figure 3:
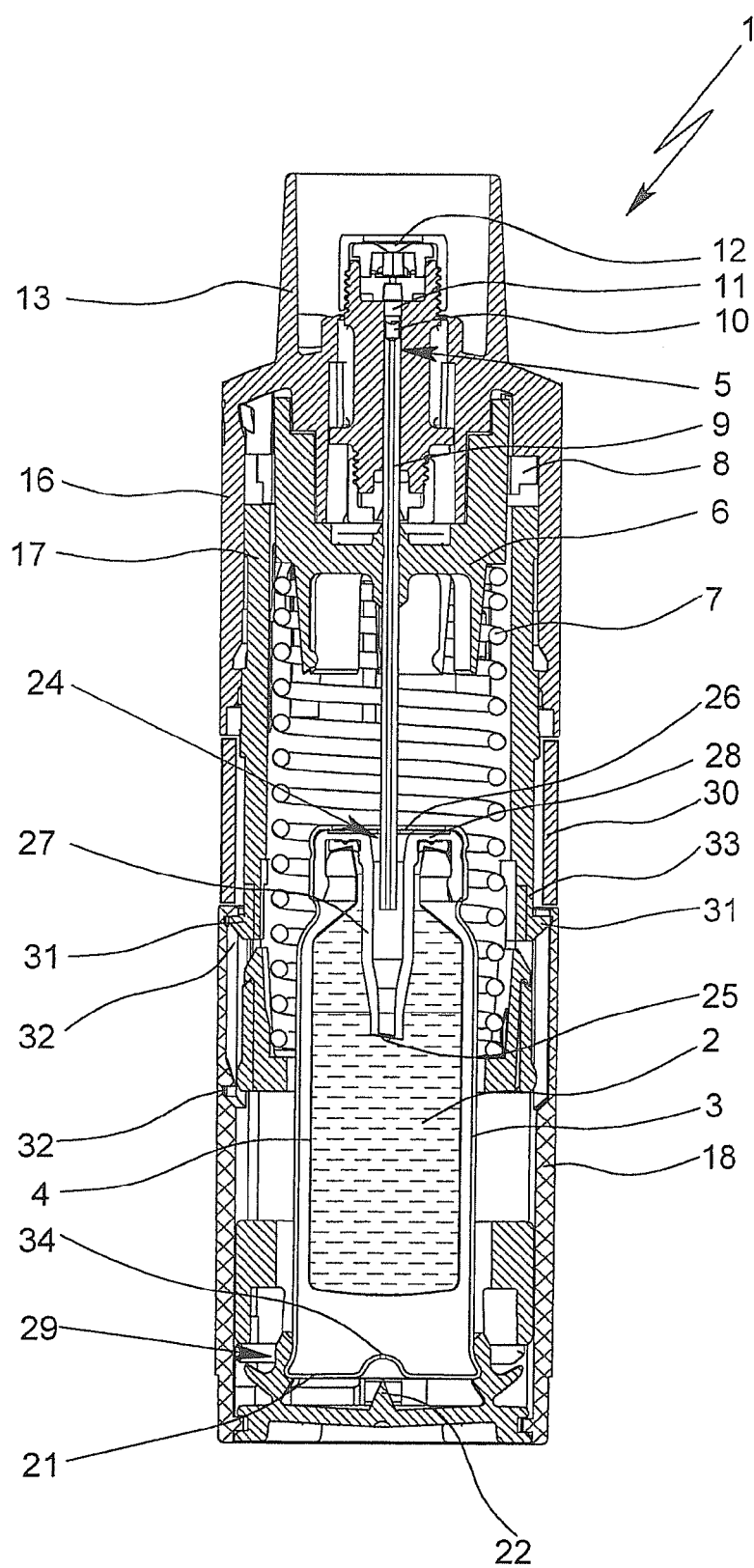
Figure 4:
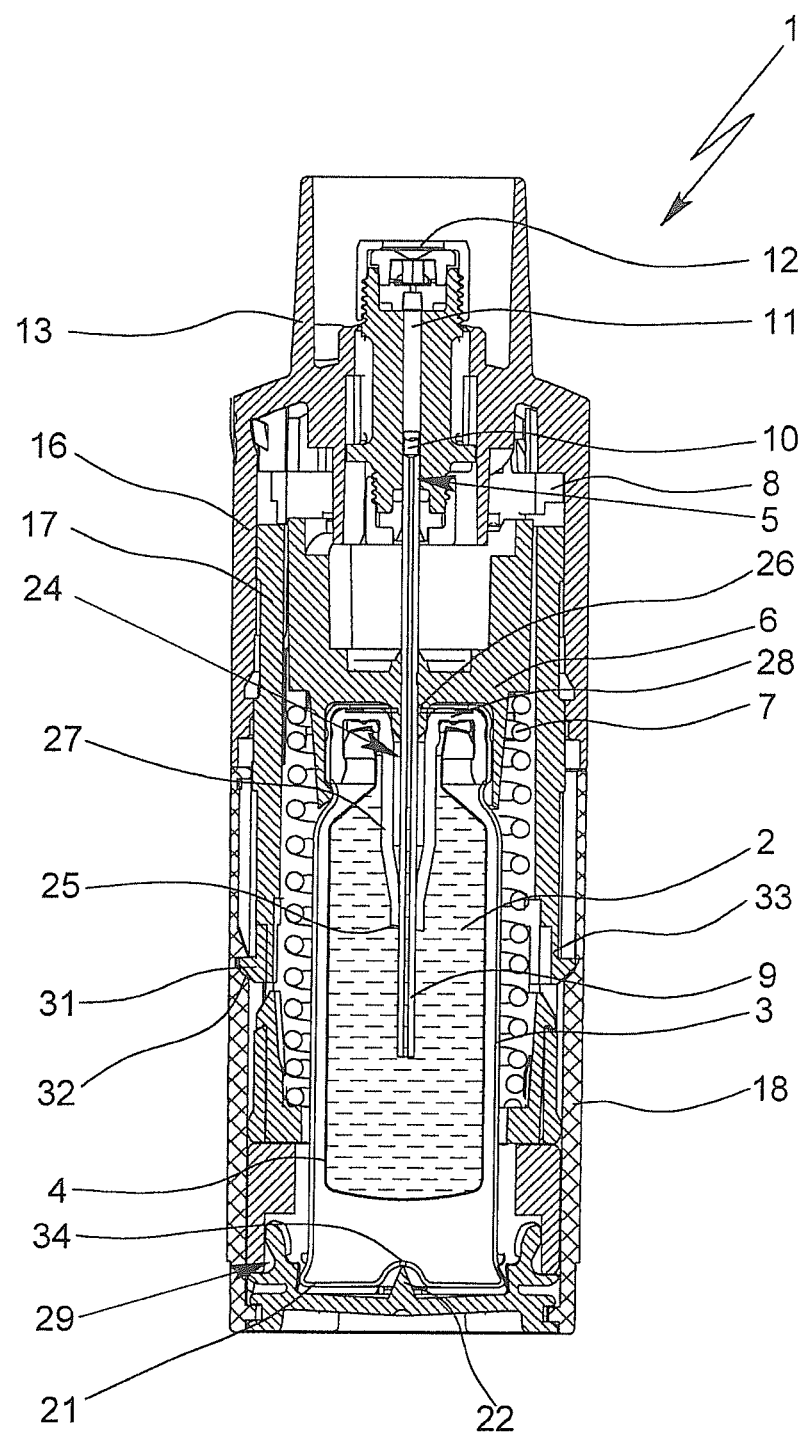
Figure 5:
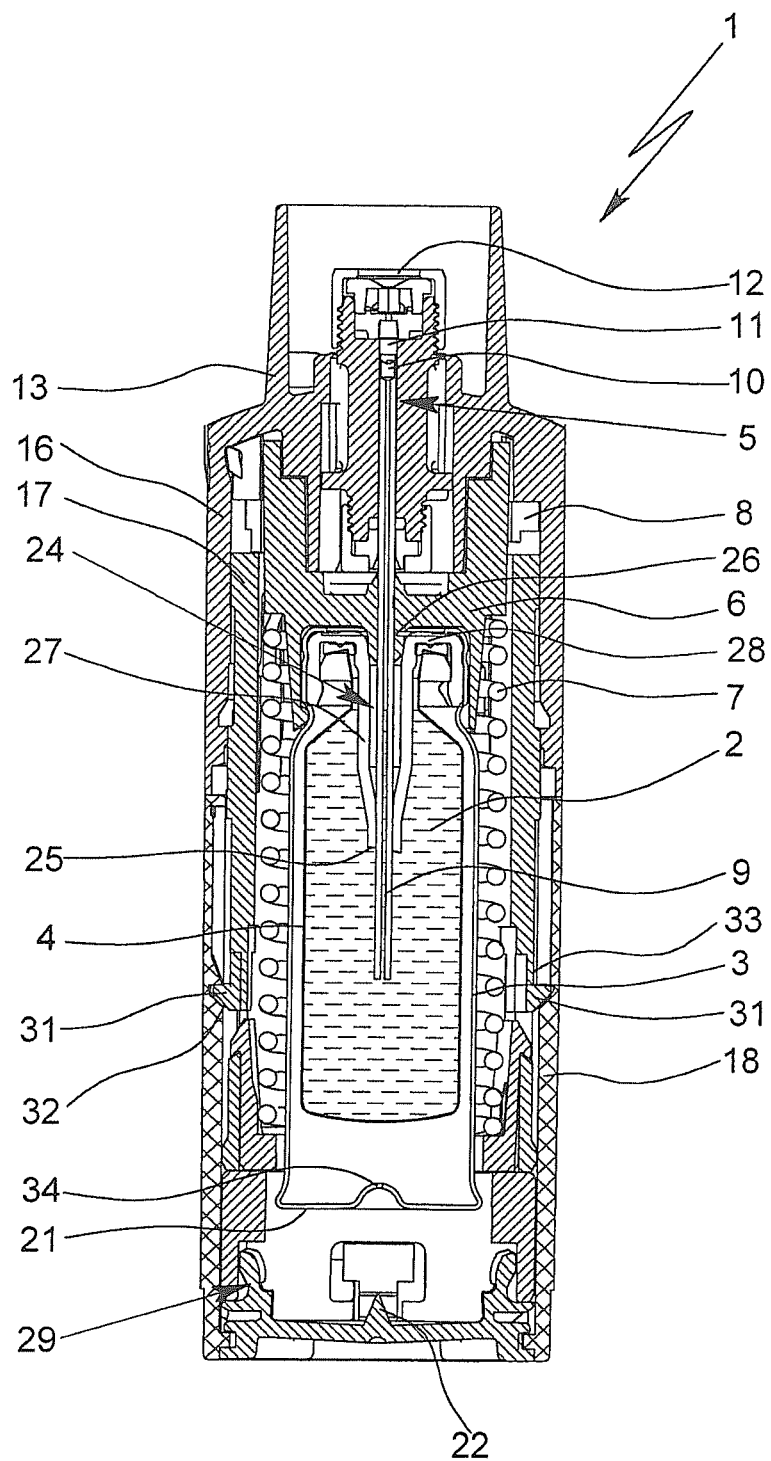
Figure 6:
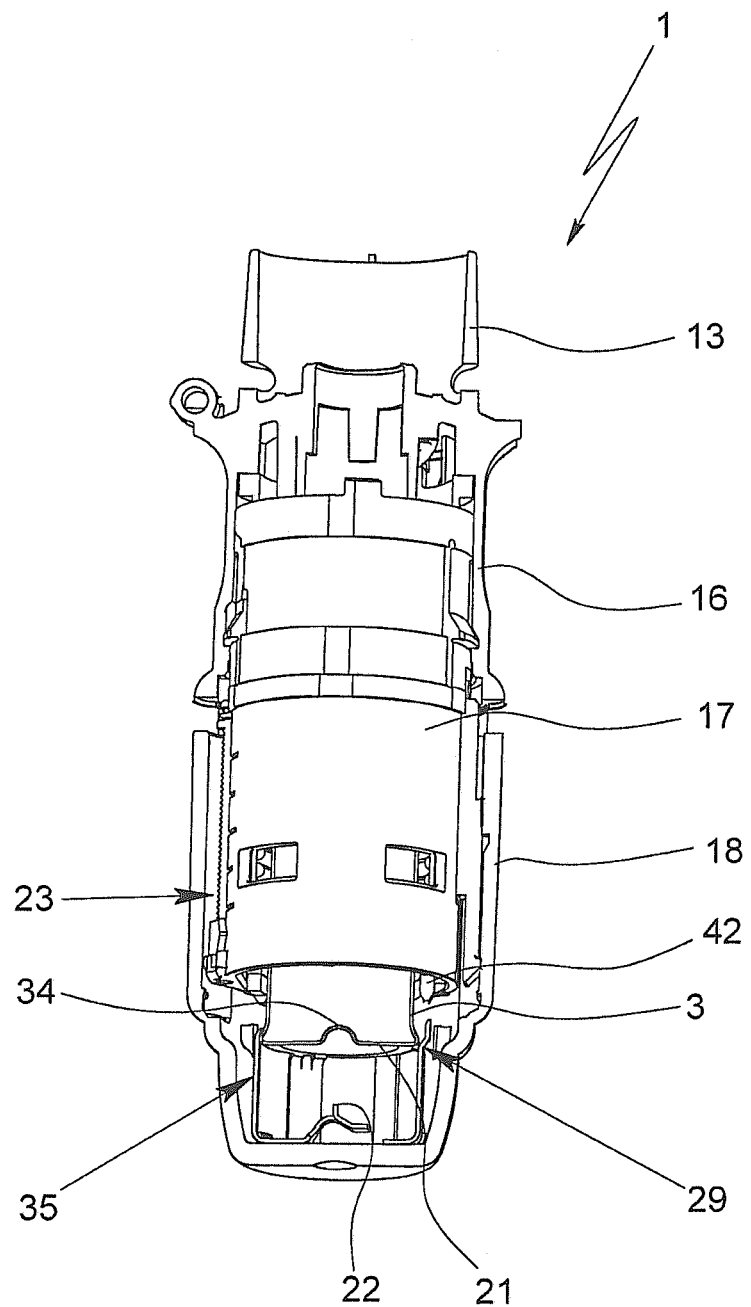
Figure 7:
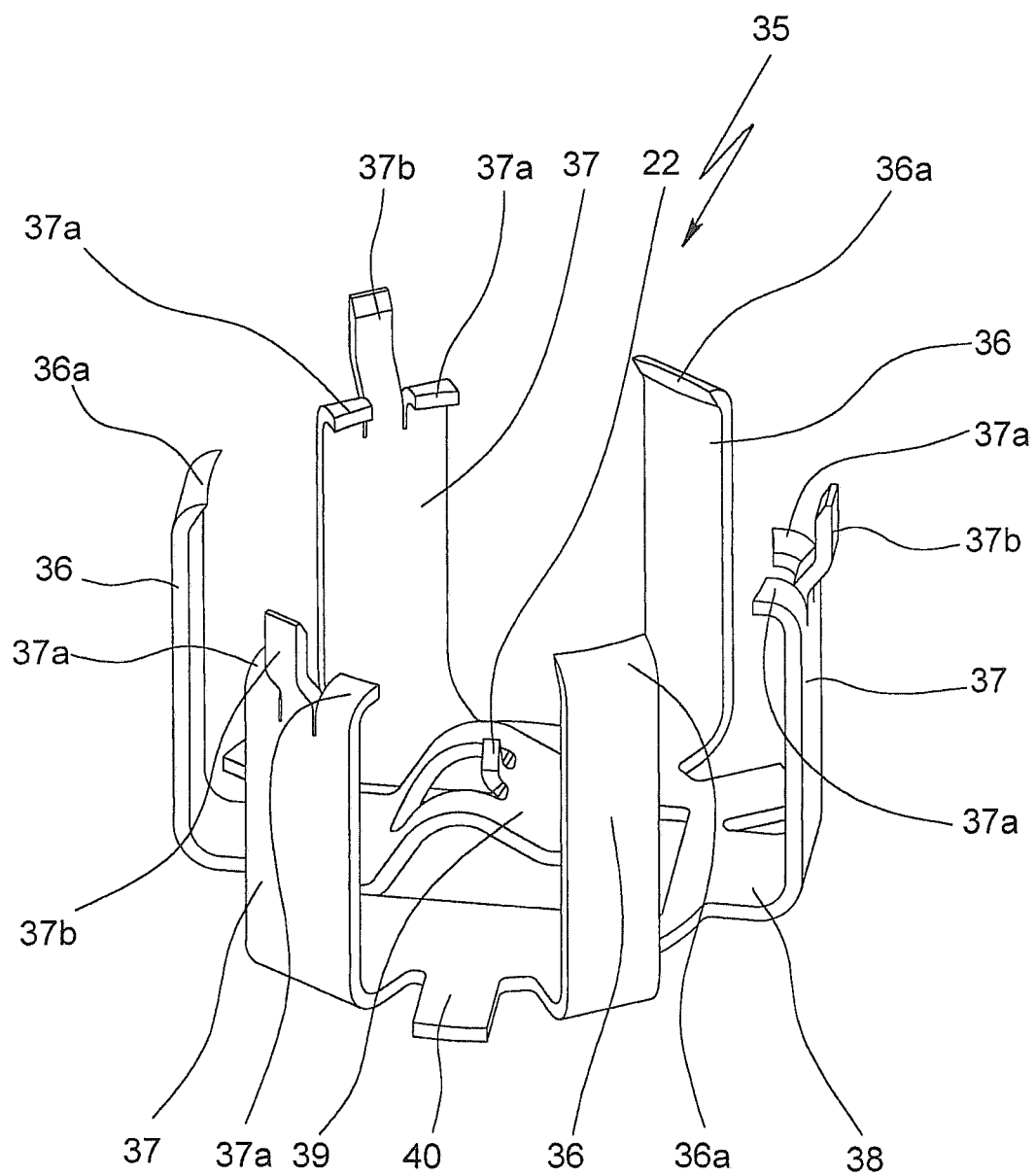
Figure 8:
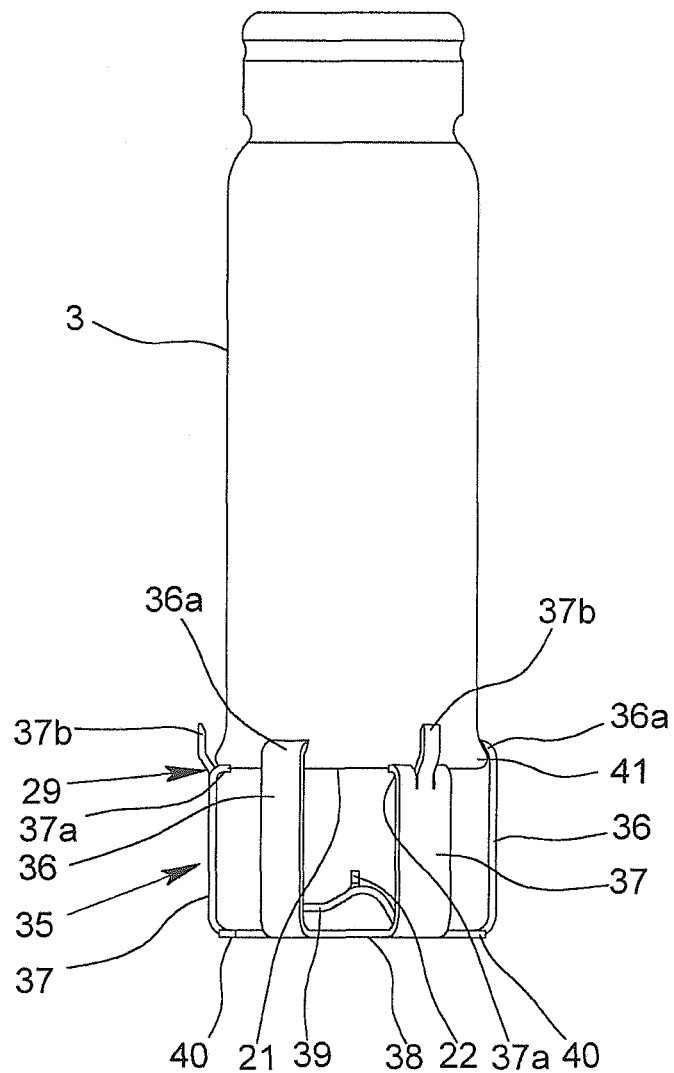
Figure 9:
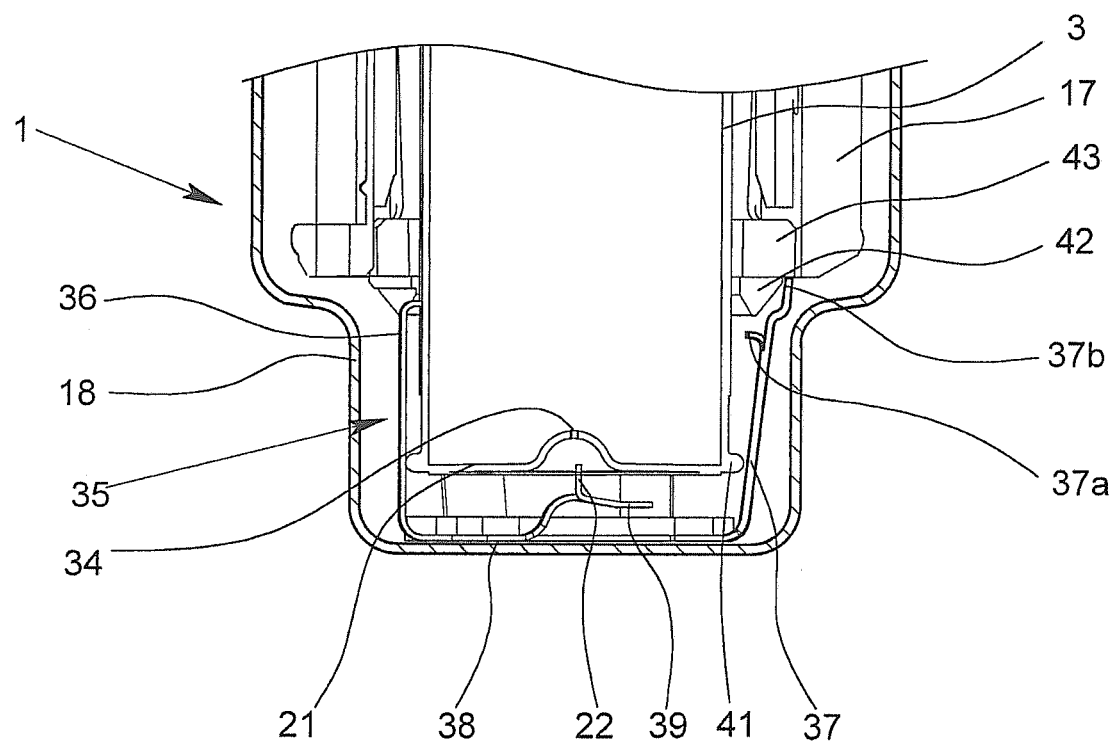
Figure 10:
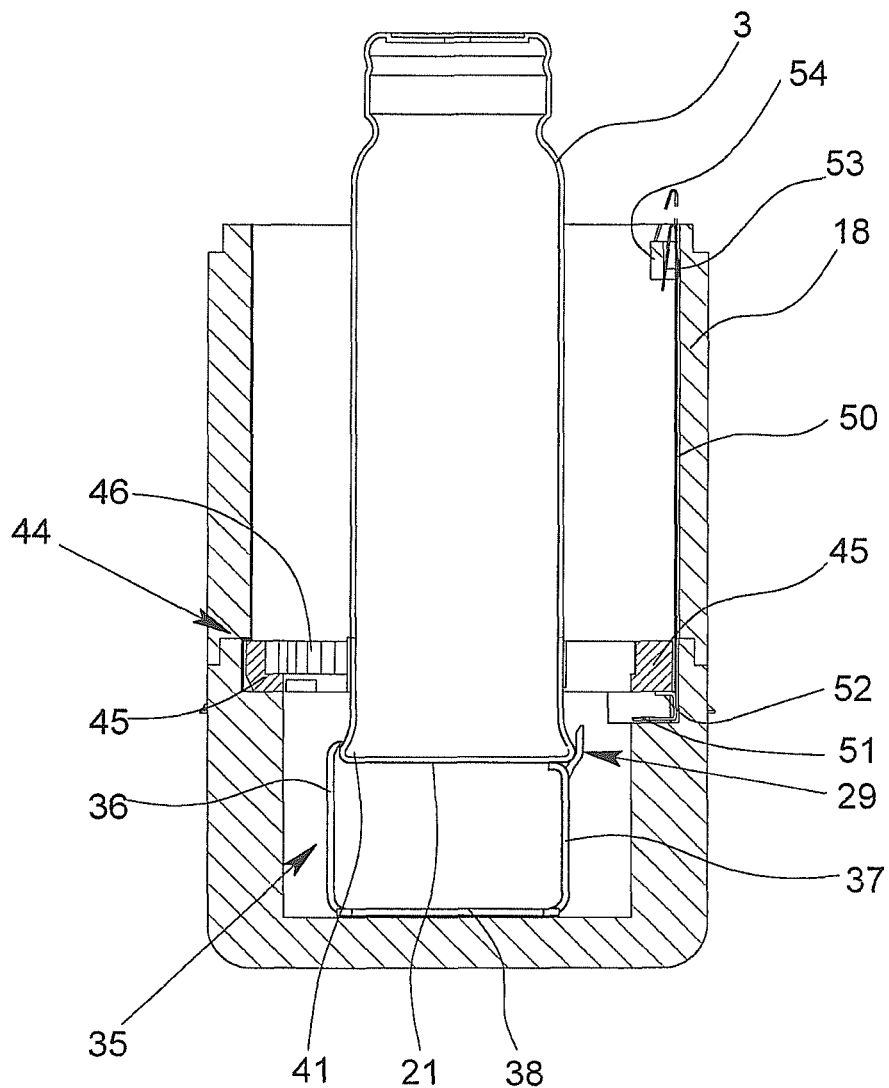
Figure 11:
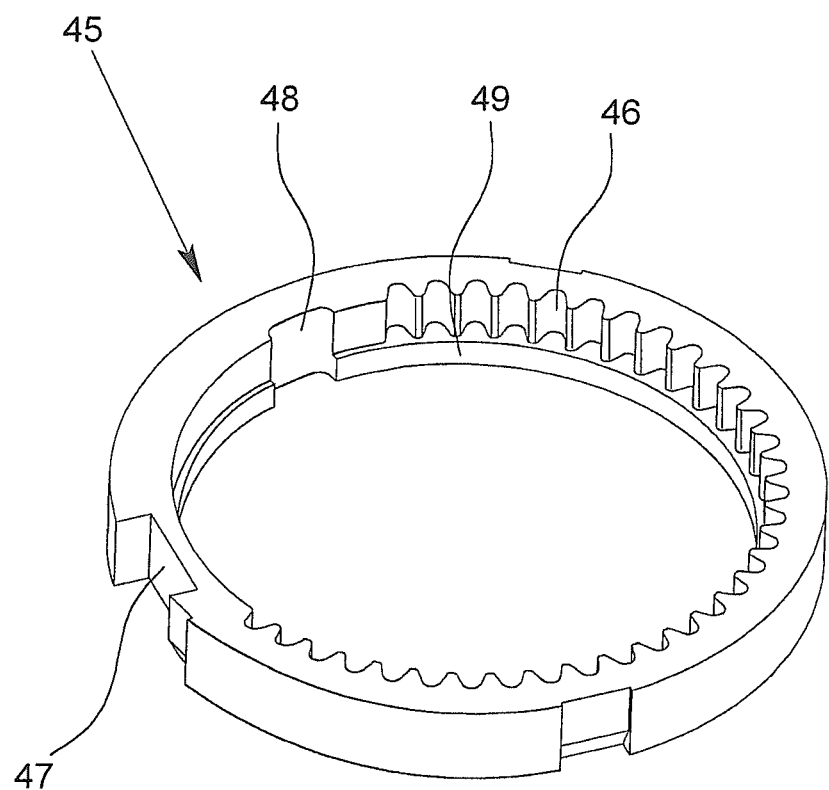
Figure 12:
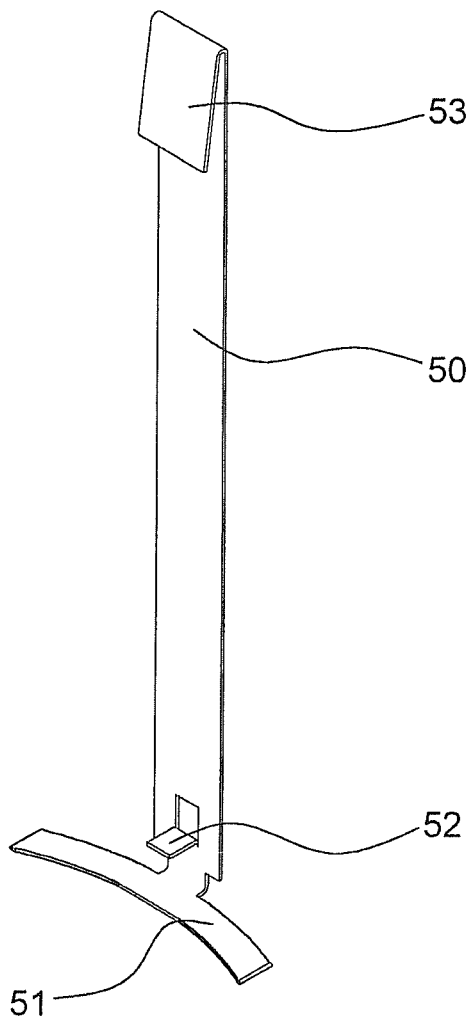
Figure 13:
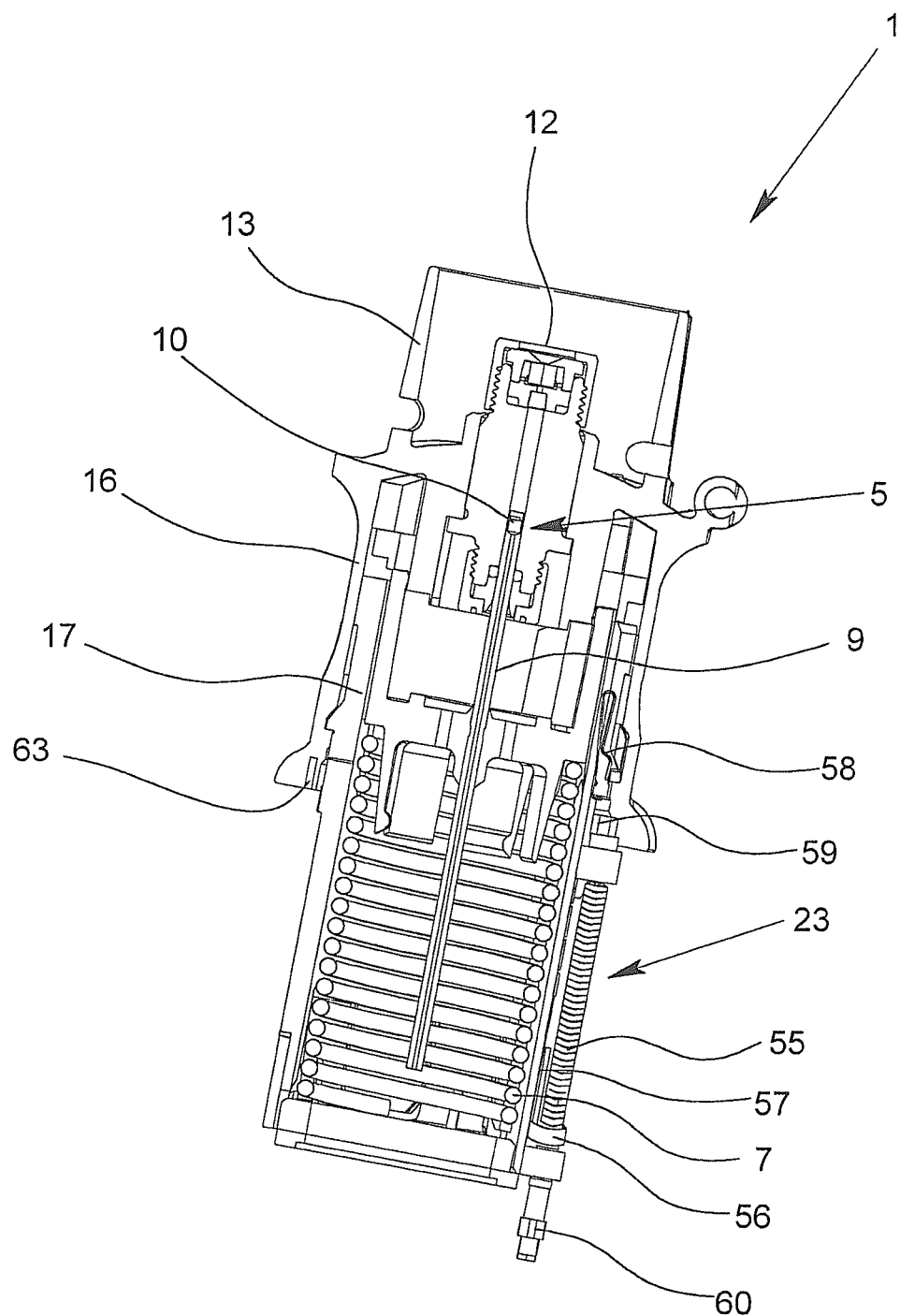
Figure 14:
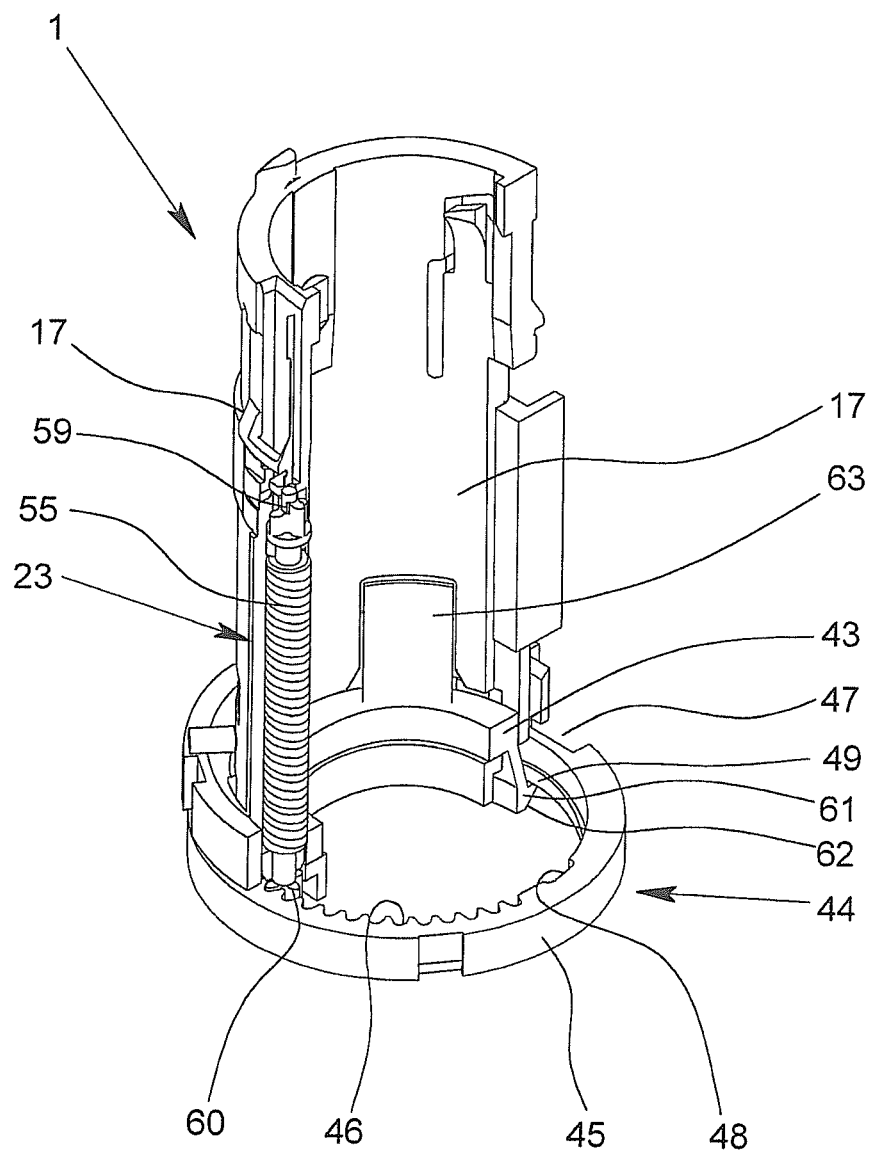

Further advantages, features, characteristics and aspects of the present invention will become apparent from the claims and the following description of a preferred embodiment with reference to the drawings. It shows:

FIG. 1 a schematic section of a known nebulizer in a non-tensioned state;

FIG. 2 a schematic section, rotated through 90° compared with FIG. 1, of the known nebulizer in a tensioned state;

FIG. 3 a schematic section of a nebulizer in a delivery state with a partly closed housing and with a pre-installed, closed container;

FIG. 4 a schematic section of the nebulizer according to FIG. 3 in an activated, tensioned state with the completely closed housing and with the opened container;

FIG. 5 a schematic section of the nebulizer according to FIG. 4 in a non-tensioned state;

FIG. 6 a schematic section of a nebulizer with a partly closed housing and with a securing means in a housing part holding unmoveably a container in the nebulizer;

FIG. 7 a perspective view of the securing means of the nebulizer according to FIG. 6;

FIG. 8 a side view of the securing means of the nebulizer according to FIG. 6 holding the associated container unmoveably;

FIG. 9 a schematic partial view of a part of the nebulizer according to FIG. 6 with opened securing means so that the container can move;

FIG. 10 a schematic section of a housing part with an associated counter device and with an associated container of a nebulizer according to the present invention;

FIG. 11 a perspective view of a control ring of the counter device;

FIG. 12 a perspective view of a control element of the counter device;

FIG. 13 a partial sectional view of the nebulizer without housing part, counter device and container; and FIG. 14 a partial view of part of the nebulizer interacting with the control ring of the counter device.

In the Figures, the same reference numerals have been used for identical or similar parts, resulting in corresponding or comparable properties and advantages, even if the associated description is not repeated.

FIGS. 1 and 2 show a known nebulizer 1 for atomizing a fluid 2, particularly a highly effective pharmaceutical composition or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which the patient is suffering.

The nebulizer 1 is provided with or comprises an insertable container 3 containing the fluid 2. The container 3 thus forms a reservoir for the fluid 2 which is to be nebulized. Preferably, the container 3 contains an amount of fluid 2 or active substance which is sufficient to provide up to 200 dosage units, for example, i.e. to allow up to 200 sprays or applications. A typical container 3, as disclosed in WO 96/06011 A1, holds e.g. a volume of about 2 to 10 ml.

The container 3 is substantially cylindrical or cartridge-shaped and once the nebulizer 1 has been opened the container can be inserted therein from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally adjustable dosage amount. The pressure generator 5 comprises preferably a holder 6 for the container 3, an associated drive spring 7, only partly shown, a locking element 8 which can be manually operated to release the spring 7, a conveying element, such as a conveying tube 9, a non-return valve 10, a pressure chamber 11 and/or an nozzle 12 for nebulizing the fluid 2 into a mouthpiece 13. The container 3 is fixed or held in the nebulizer 1 via the holder 6 such that the conveying tube 9 penetrates into the container 3. The holder 6 may be constructed so that the container 3 can be exchanged.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10 (conveying of the fluid 2, suction stroke). Then, the nebulizer 1 is in the so-called activated or tensioned state.

During the subsequent relaxation after actuation of the locking element 8 the fluid 2 in the pressure chamber 11 is put under pressure as the conveying tube 9 with its now closed non-return valve 10 is moved back upwards by the relaxation of the drive spring 7 and now acts as a pressing ram or piston (pressure generation and/or nebulization). This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, and/or with a volume of fluid 2 delivered per stroke of 10 to 50 µl, preferably 10 to 20 µl, most preferably about 15 µl. The fluid 2 is converted into or nebulized as aerosol 14, the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user (not shown) can inhale the aerosol 14, while an air supply can be sucked into the mouthpiece 13 through at least one air supply opening 15.

Preferably, the nebulizer 1 can be manually activated or tensioned. The nebulizer 1 comprises preferably an upper housing part 16 and an inner part 17 which is rotatable relative thereto (FIG. 2) having an upper part 17a and a lower part 17b (FIG. 1), while an in particular manually operable (lower) housing part 18 is releasable fixed, particularly fitted onto the inner part 17, preferably by means of a retaining element 19. Preferably, the housing parts 16 and 18 form a housing of the nebulizer 1. In order to insert and/or replace the container 3 the housing part 18 can be detached from the nebulizer 1 or its housing.

The housing part 18 can be rotated relative to the upper housing part 16, carrying with it the part 17b of the inner part 17. As a result the drive spring 7 is tensioned in the axial direction by means of a gear or transmission (not shown) acting on the holder 6. During tensioning the container 3 is moved axially downwards until the container 3 assumes an end position as shown in FIG. 2. In this activated or tensioned state the drive spring 7 is under tension. During the nebulizing process the container 3 is moved back into its original position (non-tensioned position or state shown in FIG. 1) by the drive spring 7. Thus the container 3 executes a lifting or stroke movement during the tensioning process and during the atomizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 may comprise a monitoring device 23 which counts the actuations of the nebulizer 1, preferably by detecting the rotation of the inner part 17 relative to the upper part 16 of the housing. Preferably, the monitoring device 23 blocks the actuation or use of the nebulizer 1, e.g. blocks the actuation of the locking element 8, when a certain number of actuations or discharged doses has been reached or exceeded.

A preferred construction and mode of the inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

FIGS. 3 to 5 show, in schematic sectional views, a nebulizer 1 according to a slightly different embodiment. FIG. 3 shows the nebulizer 1 in a delivery state, i.e. with pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated and/or tensioned state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after the delivery or discharge of one dose of the fluid 2; the container 3 is in its upper position.

The container 3 is already mounted or pre-installed in the nebulizer 1 in the delivery state, as shown in FIG. 3. In this state, the container 3 is still closed, i.e. there is no fluidic connection between the container 3 or its bag 4 on one hand and the nebulizer 1 or its pressure generator 5 or the conveying element on the other hand.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided to cover and/or close the fluid inlet 24.

Preferably, the closures 25 and 26 are designed such that successive opening is possible by means of one common element, in particular the conveying element or conveying tube 9 or the like, and/or by piercing.

In the preferred embodiment, the first closure 25 and second closure 26 are arranged one after the other and/or spaced in axial direction or direction of the stroke movement of the container 3 or with respect to the main outlet direction of the fluid 2.

Generally, the container 3, fluid outlet 24 or closures 25 or 26 are opened in particular by means of a conveying element, such as the conveying tube 9, or the like and/or by piercing or in any other suitable manner. In particular, the opening is achieved by moving the container 3 relative to the nebulizer 1 or conveying element or tube 9 or the like and/or by movement in longitudinal or axial direction.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state, preferably by not completely closing or pushing on the housing part 18 in the shown embodiment. Preferably, the housing part 18 is snapped on or inserted only partly in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the first closure 25, is prevented.

In the shown embodiment, the securing member 30 is preferably mounted between the housing part 18 and the upper housing part 16 and preferably engages with or between the housing parts 16 and 18, so that the housing part or lower part 18 is axially secured or is kept or held sufficiently away or spaced from the upper housing part 16 to be able to hold the (still) closed container 3 or first closure 25 away from the conveying tube 9.

In the preferred embodiment, the securing member 30 is at least substantially hollow and/or cylindrical and is disposed axially between the (lower) housing part 18 and the upper housing part 16. To activate the nebulizer 1 or prepare its for use, i.e. to push the housing part 18 fully on in the axial direction and thereby open the container 3, the securing member 30 first has to be removed or released or opened. In the shown preferred embodiment, the securing member 30 is constructed in the manner of a banderole or the like, made of plastics, for example, and/or can be manually opened, removed or destroyed. The securing member 30 may alternatively or simultaneously form or constitute a seal of origin. However, other embodiments of the securing member 30 are also possible, e.g. in the form of a security tag or the like.

Preferably, the container 3 and/or housing part 18 are held positively or in a form-fit or interlocking manner in the delivery state. This is achieved in the preferred embodiment in particular by means of the transportation lock 29 acting between the container 3 and the housing part 18, and the securing member 30 acting between the housing part 18 and the housing of the nebulizer 1 or the upper housing part 16 or the like. However, the transportation lock 29 or securing member 30 could also act directly between the container 3 on one hand and the nebulizer 1, its housing, the upper housing part 16, the inner housing part 17 or the holder 6 on the other hand.

The pre-installed container 3, i.e. its first closure 25, is still closed in the delivery state, i.e. non-activated state with pre-installed container 3.

In order to secure the housing part 18, it may be secured in the delivery state by means of at least one latching lug 31, protrusion, nose or the like which engages in an associated latching recess 32 in the housing part 18 or the like. The latching lug 31 may be formed by or at a latching arm 33 which can preferably flex.

Once the security member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9). In this pushed on or activated state, the housing part 18 is preferably secured or axially fixed by interlocking engagement, i.e. form-fit manner in axial direction, particularly by the engagement of the retaining element 19 or the like, but can be detached if desired.

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

The nebulizer 1 is activated after the removal of the securing member 30 and (total) axial pushing on of the housing part 18 and can be used in the same way as the nebulizer 1 shown in FIGS. 1 and 2.

To prevent unwanted opening of the container 3, particularly of the first closure 25, in the delivery state of the nebulizer 1, preferably the transportation lock 29 is provided. By frictional, forcible or interlocking engagement, for example, the transportation lock 29 prevents the container 3 from undesirably moving axially in the nebulizer 1, e.g. during transportation, in the event of accidental dropping of the nebulizer 1 or the like.

Preferably, the opening of the transportation lock 29 occurs automatically when closing the nebulizer 1 or its housing completely, i.e. when snapping or pushing on the housing part 18 completely towards the upper housing part 16. During this (axial or telescopic) closing movement, the transportation lock 29 is opened and the container 3 released in axial direction preferably only in a last part of the movement and/or just little before the final completely closed position is reached or just when the final completely closed position is reached.

During the closing movement the transportation lock 29 is preferably opened by the direct or indirect interaction with or actuation by the housing of the nebulizer 1, the inner part 17 or its lower part 17b, a holding ring 43 bearing the spring 7 or the like. Preferably, the container 3 and/or first closure 25 are opened as well as the transportation lock 29 by means of a common actuation, here the closing movement of the nebulizer 1 or its housing or bottom part 18.

FIGS. 4 and 5 show the transportation lock 29 in the open position, i.e. wherein the container 3 is free to move axially.

Preferably, in the non-activated state, i.e. when the housing part 18 has not been pushed on fully, the nebulizer 1 may be locked to prevent tensioning of the pressure generator 5, i.e. in particular to prevent rotation of the inner part 17 relative to the upper housing part 16. This may be important when the nebulizer 1 is supplied in the delivery state with the pressure generator 5 not under tension. Accordingly, the inhaler 1 may have a barrier, so that the inner part 17 can only be rotated relative to the upper housing part 16 when the housing part 18 has been pushed fully on. Alternatively or additionally, the securing member 30 may block not only pushing on of the bottom part 18 in the delivery state, but also any rotation of the inner part 17 until the securing member 30 has been opened, released or removed.

In the following, further aspects of the inhaler or nebulizer 1 will be described in detail with reference to FIGS. 6 to 9, wherein only essential differences will be emphasized so that the previous remarks and explications relating to the nebulizers 1 according to FIGS. 1 to 5 apply preferably in a corresponding or similar manner.

FIG. 6 shows in a very schematic, partially sectional view the nebulizer 1 in the delivery state with not completely closed housing or housing part 18. However, the housing part 18 has already been pushed on the inner part 17 more than initially provided in the delivery state such as shown in FIG. 3. Therefore, the container 3 has already been opened in the state shown in FIG. 6. Further, the securing member 30, which preferably secures the housing part 18 in the delivery state against pushing on the inner part 17, has already been released or opened or removed in the state shown in FIG. 6.

The nebulizer 1 or its housing comprises a securing means 35 for holding the container 3 such that the container 3 is moveable back and forth for the conveying of the fluid 2, pressure generation and/or nebulization, but is inseparable from the housing or housing part 18, and/or such that the container 3 is unmoveably held in the delivery state of the nebulizer 1.

The securing means 35 is located or arranged preferably at or in the housing part 18 as shown in FIG. 6.

FIG. 7 shows in a perspective view a preferred embodiment of the securing means 35. FIG. 8 shows the securing means 35 connected with the container 3.

Preferably, the securing means 35 comprises or consists of a metal and/or stamping part and/or consists of a single, unitary part as shown in FIG. 7.

Preferably, the securing means 35 is made of steel, in particular spring steel.

Preferably, the securing means 35 is produced from sheet material by cutting, stamping or the like and/or by bending.

Preferably, the securing means 35 or the part forms a cage, in particular, encompasses the container 3 or an end portion thereof.

Preferably, the securing means 35 comprises holding elements 36 and/or locking elements 37. The elements 36 and 37 are preferably designed like arms, fingers, leaves or the like. In particular, the elements 36, 37 are alternately distributed over a circumference of the container 3 and/or extend at least essentially axially or in the direction of the back and forth movement of the container 3.

Preferably, the elements 36 and 37 are held by or connected with a base 38 of the securing means 35.

Preferably, the securing means 35 or base 38 comprises or holds the piercing element 22 for piercing the container 3, i.e. opening the container base 21 or its venting hole 34 in the activated and tensioned state, i.e. when the container 3 reaches its lower end position. In the shown embodiment, the piercing element 22 is formed by a respective bending of a spring portion 39 of the securing means 35 or its base 38. The spring portion 39 can support or facilitate the (complete or final) connection of the container 3 to holder 6.

The securing means 35 or base 38 comprises preferably at least one or multiple fixing portions 40 for fixing the securing means 35 at or in the nebulizer 1 or housing or housing part 18. In particular, the fixing portions 40 may fix the securing means 35 when the securing means 35 is pressed into the housing part 18 by cooperating with the sidewall of the housing part 18. However, it is also possible to over mold the securing means 35, its base 38, the fixing portions 40 or the like. Moreover, the securing means 35 could be connected with the housing part 18 or the like in any other suitable manner.

Preferably, the securing means 35 does not only prevent the separation of the container 3 from the nebulizer 1, its housing or housing part 18, but also forms the transportation lock 29 for holding the container 3 unmovable in the housing in the delivery state of the nebulizer 1. FIGS. 6 and 8 shows this state or situation when the container 3 is held (axially) unmovable by the securing means 35, i.e. when the transportation lock 29 is closed. In this situation, the container 3 or its preferably radially protruding end or edge 41 of the container 3 is held between the holding element 36 and locking element 37, in particular between respectively formed or bent ends of the elements 36 and 37.

In the shown embodiment, the container end or edge 41 is caught between end portions 36a and 37a of the elements 36 and 37. The holding elements 36 grip or extend over the edge 41 and the locking elements 37 or its end portions 37a grip or extend under the edge 41 or container base 21 so that the edge 41 and container 3 are securely held preventing any axial movement of the container 3 relative to the securing means 35 and relative to the associated housing part 18 in this state, i.e. with locked securing means 35/transportation lock 29.

The holding element 36 and the locking elements 37 are distributed alternating around the container 3 or edge 41.

Preferably, the end portions 36a of the holding elements 36 end in a first radial plane and the end portions 37a of the locking elements 37 end in another, second radial plane, wherein the two planes are axially offset to hold the edge 41 in between and/or wherein the second plane is located axially between the first plane and the lower end position of the container 3 or the lower end of the housing part 18 or the piercing element 22. Additionally or alternatively, the end portions 36a end on another radius (outer radius) than end portions 37a and/or axially spaced.

The end portions 36a and/or 37a preferably form like claws or the like and/or extend preferably radially inwardly.

Preferably, the elements 36 and/or 37 can flex with its free ends radially outwardly.

For example, the ends of the end portions 36a may be inclined such that the container 3 may be inserted into or connected with the securing means 35 by a respective axial force so that the holding elements 36 flex outwardly to allow passing of edge 41. However, the holding elements 36 can be flexed outwardly also by a suitable tool (not shown) or the like when the container 3 is inserted, in particular with its edge 41, into the securing means 35.

Preferably, the holding elements 36 prevent separation of the container 3 from the securing means 35 and, thus, from the associated housing part 18 or the like.

The locking elements 37 or its end portions 37a can be flexed radially outwardly in order to open the axial holding or transportation lock 29 (this will be explained in detail with reference to FIG. 9 in the following). Then, the container 3 can axially move, in particular back and forth and/or with its edge 41 between the first plane and the piercing element 22 in the present embodiment.

In the present embodiment, the locking elements 37 comprise actuation portions 37b (preferably formed at the free ends and/or between adjacent end portions 37a). Preferably, the actuation portions 37b form axial extensions which may be radially offset. The actuation portion 37b cooperate with an associated control member 42 or multiple control members 42 of the nebulizer 1 such that the locking elements 37 are flexed radially outwardly when (completely) closing the housing to open the transportation lock 29 (here primarily formed by the locking elements 37 or its end portions 37*a*).

FIG. 6 shows schematically the control member 42 axially spaced from the associated actuation portion 37*b* as the housing has not yet been closed (completely).

FIG. 9 shows a lower part of the completely closed nebulizer 1 with opened transportation lock 29, i.e. with radially outwardly flexed locking elements 37. FIG. 9 shows that the control member 42 has an inclined guiding surface or the like to convert the axial closing movement into the radial opening movement of the actuation portion 37*b* and, thus, of the associated locking element 37 to open the transportation lock 29, in particular when the housing has been completely closed or when the housing part 18 has been pushed completely on the nebulizer 1.

The control member 42 is preferably formed as an axial protrusion. It can be formed by or at ring 43 or any other bearing means of the nebulizer 1 for counter-bearing the drive spring 7 in the inner part 17 or by or at any other suitable component of the nebulizer 1 such as the inner part 17.

The control member 42 may be formed like an axial protruding ring or shoulder or ridge which extends along the ring 43.

The control member 42 may additionally secure the holding elements 36 against axial opening when the housing is completely closed as schematically shown in FIG. 9. In this case, the control member 42 contacts the holding element(s) 36 or its end portions 36*a* peripherally on the outer side to prevent any outward flexing. Then, the securing means 35 or its holding elements 36 are secured against opening so that the container 3 is securely held within the securing means 35 or the cage formed by the securing means 35 or holding elements 36.

FIG. 9 shows the container 3 in its lower position when the piercing element 22 can pierce the venting hole 34 or an associated seal attached to the container base 21.

In the present embodiment, the securing means 35 has multiple functions. It holds the container 3 (in the activated state/with completely closed housing) such that it can move back and forth, in particular during conveying of the fluid 2, during pressure generation and/or during nebulization, wherein the container 3 is inseparable from the housing or the housing part 18. Further, the securing means 35 forms the transportation lock 29 and/or holds the container 3 unmovable in the delivery state of the nebulizer 1. Additionally or alternatively, the securing means 35 comprises an opening means, here the piercing element 22, for opening the venting hole 34 of the container 3.

Preferably, the securing means 35 forms a cage which cannot be separated from the container 3 after connecting it with the container 3.

The transportation lock 29 and the locking elements 37 are kept opened during the normal use of the nebulizer 1, in particular as long as the housing is (completely) closed. When the housing is opened, i.e. the housing part 18 is detached, the control member 42 may disengage from the actuation portions 37*b* so that the locking element 37 can close or flex inwardly again. Then, the locking elements 37 may grip with its end portions 37*a* over the edge 41 of the container 3 such that an additional lock is formed which prevents that the container 3 can be separated from the securing means 35/housing part 18.

The securing means 35 prevents separation of the container 3 from the housing part 18. Therefore, the container 3 can be replaced or exchanged only together with the housing part 18.

In the following, a preferred embodiment of the nebulizer 1 according to the present invention will be described with reference to FIGS. 10 to 14. The previous remarks and explications regarding FIGS. 1 to 9 apply preferably in a corresponding or similar manner. Primarily, only essential differences or new aspects will be explained in detail. The nebulizer 1 is reusable, i.e. can be used with multiple containers 3 one after the other.

The nebulizer 1 comprises a counter device 44 for counting operations of the nebulizer 1. It is preferably separate from the monitor device 23 even if the latter one drives the counter device 44 or vice versa.

The counter device 44 blocks opening of the nebulizer 1 until a predetermined number of operations has been reached or exceeded. In particular, the counter device 44 is associated to preferably only one container 3 and counts operations of the nebulizer 1 with the respective container 3, i.e. counts (only) the number of doses of fluid 2 removed or still removeable from this container 3. Thus, the counter device 44 blocks opening of the nebulizer 1 until a predetermined number of doses of the fluid 2 has been drawn or removed from the respective container 3. With other words, the counter device 44 counts the operations or uses of the respective container 3 in the nebulizer 1 and blocks opening of the nebulizer 1 until a predetermined number has been reached or exceeded.

Preferably, the counter device 44 is associated to or located at or in the container 3 and/or housing part 18. FIG. 10 shows in a schematic section the housing part 18 of the nebulizer 1, wherein the counter device 44 is attached to or located in the housing part 18, in particular, cannot be separated from the housing part 18. The container 3 is preferably inseparable from the housing part 18 and, thus, from the counter device 44 or vice versa.

The container 3 is preferably inseparably connected with the housing part 18 by means of the securing means 35 as already discussed.

In the shown embodiment, the counter device 44 comprises preferably a control means, in particular a control ring 45, which is shown separately in a perspective view in FIG. 11. The control means or control ring 45 comprises a preferably inner toothing 46, a control recess 47, a delocking recess 48 and/or a preferably inner shoulder or ridge 49. Preferably, the control means or control ring 45 is rotatable and/or is indexed each time a use or operation is counted, e.g. each time the nebulizer 1 is tensioned, the container 3 is moved, fluid 2 is drawn from the container 3, fluid 2 is nebulized, the drive spring 7 pressurizes the fluid 2, or the like.

The counter device 44 comprises preferably a control element 50 which is shown in FIG. 10 and in a perspective view in FIG. 12. The control element 50 is preferably associated to the control means or control ring 45. In the present embodiment, the control element 50 comprises a biasing portion 51, an engagement portion 52 and/or a locking portion 53. In particular, the control element 50 is axially moveable and/or guided by the housing part 18.

Preferably, the control element 50 can block the used container 3 and/or housing part 18 against further use, reuse and/or reconnection with the nebulizer 1. FIG. 10 shows the control element 50 in the initial, non-blocking position and in the dashed line in the blocking position, i.e. in the shown embodiment shifted axially and/or upwardly and/or towards upper housing part 16 not shown in FIG. 10. In particular, the control element 50 protrudes in its blocking position over the housing part 18 and/or into the upper housing part 16.

A holding portion 54, here located at or formed by the housing part 18, or the like cooperates with the locking portion 53 such that the control element 50 is locked in the blocking position once the control element 50 has reached its blocking position. With other words, the locking portion 53 enables (inversible) self-locking of the control element 50 in the blocking position.

The counter device 44 is preferably driven by the monitoring device 23 of the nebulizer 1. This will be explained in the following before a detailed description of the function of the counter device 44 follows.

FIG. 13 shows in a schematic partial section of the nebulizer 1a preferred basic construction of the monitoring device 23. In the present embodiment, the monitoring device 23 comprises a drive element, here a threaded shaft 55, with an associated rider 56. When rotating the drive element or threaded shaft 55, the rider 56 is axially moveable wherein the axial position of the rider 56 corresponds to the total number of operations or actuations of the nebulizer 1 and/or to the number of containers 3.

When the nebulizer 1 reaches or exceeds a predetermined value of operations or actuations, the monitoring device 23 or an actuation portion 57 of the rider 56 can lock the nebulizer 1 against further operation or use, in particular by interlocking the inner part 17 with the upper housing part 16 or vice versa. This is realized in the shown embodiment in that the actuation portion 57 of the rider 56 cooperates with or actuates a locking spring 58, in particular axially shifts the locking spring 58. The locking spring 58 is mounted in a pre-tensioned state such that it can radially expand and engage into a radial recess or the like when the locking spring 58 or part thereof is actuated or axially shifted (here by the rider 56 or its actuation portion 57) to lock the nebulizer 1 or interlock its parts 16 and 17. However, other constructional solutions are possible as well.

The monitoring device 23 is preferably driven by the rotation of the inner part 17 relative to the upper housing part 16 when tensioning the nebulizer 1. In the present embodiment, the monitoring device 23 or its shaft 55 is connected to or held by the inner part 17. The monitoring device 17 or shaft 55 comprises a drive gear 59 which meshes with the upper housing part 16 so that the shaft 55 is rotated when the nebulizer 1 is tensioned or the inner part 17 is rotated relative to the upper housing part 16. In particular, the drive gear 59 is directly connected with or formed by the shaft 55. However, other constructional solutions are possible as well.

Preferably, the tensioning of the nebulizer 1 or the rotation of the inner part 17 relative to the housing part 16 also drives the counter device 44. In particular, the monitoring device 23 or the shaft 55 drives the counter device 44 or its control member or control ring 45, preferably via a drive gear 60. In the present embodiment, the shaft 55 is axially extended and/or the drive gear 60 is connected with the shaft 55, so that the shaft 55 and/or drive gear 60 extend into the lower housing part 18 and/or mesh with the control member or ring 45, in particular its toothing 46. This cooperation is schematically shown in the schematic view of a part of the nebulizer 1 and of the counter device 44 or control ring 45 in FIG. 14. The rider 56, the locking spring 58, the upper housing part 16, the lower housing part 18 and the control element 50 are not shown in FIG. 14.

The inner toothing 46 is preferably axially open to enable an axial connection and disconnection with the associated drive gear 60 as shown in FIG. 14.

The counter device 44 blocks opening of the nebulizer 1 until a predetermined number of operations (with the respective container 3) has been reached or exceeded. For this purpose, the lower housing part 18 is blocked, in particular in a form-fit manner, against opening until the predetermined number has been reached or exceeded. This is achieved in the present embodiment by a preferably hook-like locking member 61 associated to the nebulizer 1 or its inner part 17, here connected to the ring 43 or to the free or lower end of the inner part 17. Preferably, the locking member 61 is formed unitary with or by the ring 43. However, other constructional solutions are possible as well.

When the housing of the nebulizer 1 is completely closed, i.e. the lower housing part 18 is completely pushed on the inner part 17, the nebulizer 1, in particular the locking member 61, interlocks preferably automatically with the lower housing part 18, the counter device 44 or its control ring 45. This can be achieved in that the locking member 61 flexes radially, in particular inwardly due to the interaction of a respectively inclined guiding surface 62 with the control ring 45 or ridge 49. Then, the locking member 61 has passed the control ring 45 or ridge 49, it can flex back and grip under the control ring 45 or ridge 49 so that the nebulizer 1 or its housing is blocked against opening (this state is also called blocking state or secured state).

As schematically shown in FIG. 14, the locking member 61 interlocks with the control member or ring 45, in particular the ridge 49, such that axial separation of the control ring 45, counter device 44 and/or lower housing part 18 from the inner part 17, the upper housing part 16 or the rest of the nebulizer 1 for opening the nebulizer 1 is not possible in this secured state blocking opening of the nebulizer 1.

As already mentioned, the control member or ring 45 is driven by the monitoring device 23 or shaft 55, in particular by drive gear 60 meshing with the toothing 46. Thus, the control member or ring 45 is indexed by one step each time the nebulizer 1 is used or tensioned. During this rotation of the control member or ring 45, the nebulizer 1 remains blocked against opening, in particular by the continued engagement of the locking member 61 with the circumferentially extending ride 49. When the predetermined number of operations is reached or exceeded, the delocking recess 48 reaches the locking member 61 and, thus, unblocks the nebulizer 1 so that the nebulizer 1 or its housing part 18 can be opened (axially pulled from the inner part 17, in particular when or after depressing the retaining element 19). This unblocking is possible, because the delocking recess 48 terminates the form-fit interlocking of the locking member 61 with the control ring 45 or its ridge 49 so that the locking member 61 can move through the delocking recess 48 and pass the ring 45/ridge 49 when axially detaching the lower housing part 18 together with the counter device 44 and control ring 45.

Preferably, the counter device 44 does not only block the nebulizer 1 against opening until the predetermined number has been reached or exceeded, but also provides a container controlled blocking (CCB). The CCB results in that the nebulizer 1, the container 3 and/or housing part 18 are blocked against further use or actuation with the respective container 3 when the predetermined number of operations or uses has been reached or exceeded. With other words, when a predetermined number of doses has been removed or drawn from the respective container 3, the CCB provided by the counter device 44 blocks the nebulizer 1 against further use or actuation with this container 3. Further, the container 3, the respective housing part 18 and/or the counter device 44 (which are preferably inseparably connected or form an inseparable group of components) are blocked against reuse and/or reconnection with the nebulizer 1. Thus, an empty or used container 3 is blocked against reuse and/or reconnection with the nebulizer 1.

The interlocking of the housing part 18 with the nebulizer 1 is preferably released or unblocked when CCB is reached or activated or vice versa.

In the present embodiment, the CCB is realized by means of the control element 50. The control element 50 is biased into its blocking position, preferably axially upwardly, by the biasing portion 51. For this purpose, the biasing portion 51 is preferably pre-tensioned and/or respectively preformed, e.g. V-like or curved with its free ends preferably downwardly in FIG. 12. The engagement portion 52 holds the control element 50 in the unblocking position shown in FIG. 10, in particular in that the engagement portion 42 abuts an axial face or the underside of the control member or ring 45.

When the predetermined number of operations or uses has been reached or exceeded, the control member has been indexed, i.e. the control ring 45 has been rotated, so that the control recess 47 reaches the control element 50 or engagement portion 52. Then, the engagement portion 52 can move axially into or through the control recess 47 and the control element 50 can move axially by the biasing force of biasing portion 51 so that the control element 50 moves from the unblocking position into the blocking position shown in dashed lines in FIG. 10. In this blocking position, the control element 50 protrudes over the housing part 18 and/or axially extends into a respective recess 63, slit or the like in the upper housing part 16 so that the housing part 18 is blocked against rotation relative to the upper housing part 16, i.e. so that the nebulizer 1 cannot be tensioned anymore. This blocking recess 63 is schematically shown in FIG. 13.

The control element 50 or its engagement portion 52 blocks the control ring 45 against further rotation, because the engagement portion 52 engages into the control recess 52 in the blocking position of the control element 50.

The control element 50 is locked in its blocking position preferably by locking portion 53. The locking portion 53 is held by the holding portion 54 in a compressed or radially pre-tensioned state when the control element 50 is in the unblocking position (lower axial position in FIG. 10). When the control element 50 is moved (in FIG. 10 axially upwards) into its blocking position, the locking portion 53 passes the holding portion 54 and can flex radially (here inwardly) and lock—e.g. by engagement with or abutting on the holding portion 54—the control element 50 against axial downward movement, so that the control element 50 is locked in its blocking position. This situation is shown in dashed lines in FIG. 10. However, other constructional solutions are possible as well.

When the predetermined number of operations or uses have been reached, i.e. in the unblocked state, the CCB is activated and the nebulizer 1 is not blocked against opening anymore and the nebulizer 1 is blocked against further use or tensioning. In this unblocked state, the lower housing part 18 may be detached together with the respective container 3 and the counter device 44. As already mentioned, the housing part 18 is preferably inseparable from the container 3 or vice versa. Further, the counter device 44 is preferably inseparable from the container 3 and/or housing part 18 or vice versa. Preferably, the housing part 18 is held by an appropriate force or force-fit in the unblocked state at the housing so that it is not just falling down, but this force is not too high that it can be overcome for detaching the housing part 18.

Then, a new housing part 18 may be connected together with a new container 3 and a new counter device 44 to the nebulizer 1. The nebulizer 1 may be used further with the new container 3.

The counter device 44 or its control element 50 may have also the additional function or characteristic that reconnection of the already used container 3/housing part 18 is prevented after the housing part 18 and container 3 have been detached from the nebulizer 1, or after the nebulizer 1 or its housing has been opened at least partly. To achieve this additional function, the control member 50 may move from its unblocking position to its blocking position in two steps.

In the first step, when the predetermined number of operations of the nebulizer 1 with the respective container 3 has been reached or exceeded, the control element 50 moves from its initial unblocking position not directly into the final blocking position, but into an intermediate position. The control element 50 engages in this intermediate position into the blocking recess 63 and preferably is restricted against further axial movement by the blocking recess 63, or any other means. In this intermediate position, the locking portion 53 has not yet passed the holding portion 54 (completely). Thus, the nebulizer 1 is already blocked against further use operation, in particular against tensioning or rotation of the lower housing part 18, by the control element 50 engaging into the blocking recess 63.

When the housing part 18 is detached from the nebulizer 1, the second step is performed. The control element 50 moves further axially into the blocking position shown in FIG. 10 so that the locking portion 53 passes the holding portion 54 and can flex radially as shown by the dashed line. In this final position, the control element 50 protrudes axially more than in the intermediate position. This further axial protrusion prevents that the detached housing part 18 can be attached again, because the control element 50 prevents complete closing of the housing, in particular that the already used and previously detached housing part 18 can be pushed on the inner part 17 (again) completely. Thus, the counter device 44 and/or control element 50 prevent also reconnection or reuse of the already used housing part 18 and/or already used container 3 with the nebulizer 1.

The nebulizer 1 or monitoring device 23 provides a live span blocking (LSB) when the total number of operations or uses of the nebulizer 1 has reached or exceeded the predetermined value (LSB value). The LSB is realized in the present embodiment by the locking spring 58 which finally locks the nebulizer 1 against further use, in particular against further tensioning.

As long as a LSB value has not been reached or exceeded, the monitoring device 23 does not lock the nebulizer 1 against further use. Therefore, the nebulizer 1 can be used with multiple container 3, e.g. 2, 3, 4 or 5 containers 3, one after the other until the LSB value is reached or exceeded and the nebulizer 1 is locked against further use.

In the present embodiment, the axial position of the rider 56 or of an associated display mark or the like corresponds to the total number of operations or uses of the nebulizer 1 and/or to the number of containers 3 used with the nebulizer 1 and can be made visible for the user (e.g. the lower housing part 18 is preferably transparent so that the rider 56 is directly visible from the outside in the present embodiment).

The monitoring device 23 can display or indicate the number of operations or uses already performed or still left. Further, the monitoring device 23 can display or indicate the number of containers 3 that have already been used or that can still be used.

In contrast, the counter device 44 counts only the number of operations or uses of the nebulizer 1 with the respective container 3. The rotatable position of the control member or ring 45 corresponds to this number and can be made visible for a user (not shown) if desired.

The counter device 44 can display or indicate the number of operations or uses of the nebulizer 1 with the respective container 3 already performed or still possible.

The counter device 44 and/or the monitoring device 23 can indicate or display the respective number by numerals and/or any other kind of marking, such as a color code or change, letters or the like.

Due to the inseparable interconnection of the container 3 with the housing part 18, the housing part 18 has to be replaced each time the container 3 is replaced.

Preferably, the counter device 44 consists of only up to two pars, here the control ring 45 and the control member 50.

The control ring 45 is preferably molded and/or made of plastics.

The control element 50 is preferably a stamping or bent or unitary part and/or made of metal, in particular steel or spring steel.

Generally, it should be pointed out that in the proposed nebulizer 1 the container 3 can preferably be inserted, in the nebulizer 1. Consequently, the container 3 is preferably a separate component. However, the container 3 may theoretically be formed directly by part of the nebulizer 1 or its housing part 18 or may otherwise be integrated in the nebulizer 1 or its housing part 18.

As already mentioned, individual features, aspects and/or principles of the embodiments described may also be combined with one another as desired and may be used particularly in the nebulizer according to FIGS. 1 and 5 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/047173 A2 which is incorporated herewith by reference. As already stated, these may be aqueous or non-aqueous solutions, mixtures, formulations containing ethanol or free from solvent, or the like.

LIST OF REFERENCE NUMERALS

1 nebulizer
2 fluid
3 container
4 bag
5 pressure generator
6 holder
7 drive spring
8 locking element 9 conveying tube
10 non-return valve
11 pressure chamber
12 nozzle
13 mouthpiece
14 aerosol
15 air supply opening
16 upper housing part
17 inner part
17a upper part of the inner part
17b lower part of the inner part
18 housing part (lower part)
19 retaining element
20 spring
21 container base
22 piercing element
23 mounting device
24 fluid outlet
25 first closure
26 second closure
27 closure part
28 flange
29 transportation lock
30 securing member
31 latching lug
32 latching recess
33 latching arm
34 venting hole
35 securing means
36 holding element
36a end portion
37 locking element
37a end portion
37b actuation portion
38 base
39 spring portion
40 fixing portion
41 edge
42 control member
43 ring
44 counter device
45 control ring
46 toothing
47 control recess
48 delocking recess
49 ridge
50 control element
51 biasing portion
52 engagement portion
53 locking portion
54 holding portion
55 threaded shaft
56 rider
57 actuation portion
58 locking spring
59 drive gear
60 drive gear
61 locking member
62 guiding surface
63 blocking recess

What is claimed is:

1. A nebulizer for dispensing a fluid comprising:
an insertable container containing the fluid,
a housing assembly configured to permit opening of the nebulizer for replacing the container, and
a counter device configured to: (i) count respective operations of the nebulizer, (ii) lock the nebulizer to prevent opening of the nebulizer continuously and without interruption during and through a plurality of successive operations of the nebulizer and without unlocking the nebulizer during such continuous lock to permit opening and replacing the container between any of the plurality of successive operations of the nebulizer, and until a predetermined number of the respective operations has been reached or exceeded, where the predetermined number of the respective operations is a greater plurality of operations than the plurality of successive operations of the nebulizer, and (iii) unlock the nebulizer to permit opening the nebulizer to replace the insertable container when the predetermined number of operations has been reached or exceeded,
wherein the counter device operates to continuously lock the nebulizer without interruption during and through the plurality of successive operations until the predetermined number of the respective operations has been reached or exceeded.

2. The nebulizer according to claim 1, wherein the counter device or part thereof is inseparable from the container, and/or the counter device has to be replaced together with the container, and/or the counter device counts only operations of the nebulizer with respect to one container at a time.

3. The nebulizer according to claim 1, wherein the opening of the nebulizer is blocked in form fit manner by the counter device, until the predetermined number of operations has been reached or exceeded.

4. The nebulizer according to claim 1, wherein the nebulizer is constructed as an inhaler for medical aerosol treatment.

5. The nebulizer according to claim 1, wherein the housing assembly includes a housing part configured to be detached or opened for replacing the container.

6. The nebulizer according to claim 5, wherein the housing part has to be replaced each time the container is replaced.

7. The nebulizer according to claim 5, further comprising a securing mechanism operating to hold the container in the housing part inseparably, wherein the container is moveable back and forth within the nebulizer and/or relative to the housing part during conveying of the fluid, pressure generation and/or nebulization.

8. The nebulizer according to claim 5, wherein the counter device interlocks the housing part with the nebulizer until the predetermined number of operation has been reached or exceeded, wherein the interlocking is terminated when the predetermined number of operations has been reached or exceeded so that the housing part is detachable or may be opened for replacing the container.

9. The nebulizer according to claim 5, wherein the container is inseparable from the housing part.

10. The nebulizer according to claim 9, wherein the housing part having an empty or used container and has been detached from the nebulizer is blocked against reconnection with the nebulizer.

11. The nebulizer according to claim 1, further comprising:
a plurality of the insertable containers, where one of the insertable containers is contained within the nebulizer at a time; and
a monitoring device for counting a total number of operations of the nebulizer including all of the containers.

12. The nebulizer according to claim 11, wherein the monitoring device locks the nebulizer against further operation or use when the total number of operations has reached or exceeded a predetermined value.

13. The nebulizer according to claim 11, wherein the monitoring device drives the counter device, and the counter device is separable from the monitoring device for replacement.

14. The nebulizer according to claim 1, wherein the counter device comprises a rotatable control ring, for controlling blocking of opening of the nebulizer and/or for blocking an associated container or housing part against further use and/or reconnection with the nebulizer after the container or housing part has been detached from the nebulizer.

15. The nebulizer according to claim 14, wherein the control ring comprises an axial recess with which an associated control element is engaged to lock the nebulizer against further use operation, respectively when the predetermined number of operations has been reached or exceeded.

16. The nebulizer according to claim 1, wherein the counter device comprises a control means for controlling the lock and unlock the nebulizer in such way that the counter device blocks opening of the nebulizer until the predetermined number of operations has been reached or exceeded and unblocks opening of the nebulizer when the predetermined number of the respective operations has been reached or exceeded.

17. The nebulizer according to claim 16, wherein:

the housing assembly comprises a housing part (18) which is axially detachable from the nebulizer, when the nebulizer is unlocked, in order to replace the container;

the control means is rotatable and comprises a shoulder or ridge (49) and a unlocking recess (48); and the counter includes a locking member (61) which interlocks with the shoulder or ridge (49) in a form-fit interlocking manner before the predetermined number of respective operations has been reached or exceeded, and when the predetermined number of operations is reached or exceeded, the unlocking recess (48) reaches the locking member (61) and terminates the form-fit interlocking of the locking member (61) with the shoulder or ridge (49) so that the locking member (61) is permitted to move through the unlocking recess (48) while the housing part (18) is axially detached from the nebulizer.

* * * * *